(12) United States Patent
Hershey et al.

(10) Patent No.: US 7,625,207 B2
(45) Date of Patent: Dec. 1, 2009

(54) YANKAUER SUCTION DEVICE WITH SLEEVE AND WIPER

(75) Inventors: Adrienne A. Hershey, Cumming, GA (US); Gerry Arambula, Duluth, GA (US); Scott M. Teixeira, Cumming, GA (US); Mike Sleva, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 191 days.

(21) Appl. No.: 11/640,114

(22) Filed: Dec. 15, 2006

(65) Prior Publication Data

US 2008/0145815 A1 Jun. 19, 2008

(51) Int. Cl.
*A61C 17/06* (2006.01)

(52) U.S. Cl. .............. 433/91; 433/92; 433/95; 433/99; 433/100; 604/35; 604/131; 604/171; 604/902

(58) Field of Classification Search .......... 433/91, 433/92, 95, 99, 100; 604/73, 77, 93.01, 35, 604/128, 131, 164.04, 164.01, 163, 171, 604/198, 902; 600/121
See application file for complete search history.

(56) References Cited

U.S. PATENT DOCUMENTS

| | | | |
|---|---|---|---|
| 1,120,549 A * | 12/1914 | Schellberg | 604/171 |
| 1,581,508 A | 4/1926 | Bomhard | |
| 3,894,540 A * | 7/1975 | Bonner, Jr. | 604/171 |
| 3,902,500 A | 9/1975 | Dryden | |
| 4,058,896 A * | 11/1977 | Moore | 433/91 |
| D264,246 S | 5/1982 | Ekbladh et al. | |
| 4,397,640 A | 8/1983 | Haug et al. | |
| 4,468,217 A | 8/1984 | Kuzmick et al. | |
| 4,741,326 A | 5/1988 | Sidall et al. | |
| 5,073,164 A | 12/1991 | Hollister et al. | |
| 5,083,561 A | 1/1992 | Russo | |
| 5,125,893 A | 6/1992 | Dryden | |
| 5,134,996 A | 8/1992 | Bell | |
| 5,140,983 A | 8/1992 | Jinotti | |
| 5,149,326 A | 9/1992 | Woodgrift et al. | |
| 5,220,916 A | 6/1993 | Russo | |
| 5,254,098 A | 10/1993 | Ulrich et al. | |

(Continued)

FOREIGN PATENT DOCUMENTS

JP 4054960 2/1992

(Continued)

OTHER PUBLICATIONS

International Search Report and Written Opinion, Mar. 11, 2008.

*Primary Examiner*—Cris L Rodriguez
*Assistant Examiner*—Michael R Ballinger
(74) *Attorney, Agent, or Firm*—Dority & Manning, P.A.

(57) ABSTRACT

A suction device includes an elongated suction tube having a suction tip at a distal end thereof, and a proximal end that is connectable to a suction source. A collar is slidable along the suction tube from a retracted position to a deployed position. A sleeve is provided having a proximal end fixed relative to the proximal end of the suction tube, and a distal end configured with the collar so as to move therewith and cover the suction tube in the deployed position of the collar. A wiper seal is contained within collar in sliding frictional engagement around the suction tube.

6 Claims, 4 Drawing Sheets

U.S. PATENT DOCUMENTS

| | | | |
|---|---|---|---|
| 5,325,850 A | 7/1994 | Ulrich et al. | |
| 5,333,606 A | 8/1994 | Schneider et al. | |
| 5,343,857 A | 9/1994 | Schneider et al. | |
| 5,349,950 A | 9/1994 | Ulrich et al. | |
| 5,370,610 A | 12/1994 | Reynolds | |
| 5,460,613 A | 10/1995 | Ulrich et al. | |
| 5,464,397 A | 11/1995 | Powers, Jr. | |
| 5,490,503 A | 2/1996 | Hollister | |
| 5,513,628 A | 5/1996 | Coles et al. | |
| 5,582,161 A | 12/1996 | Kee | |
| 5,582,165 A | 12/1996 | Bryan et al. | |
| 5,598,840 A | 2/1997 | Iund et al. | |
| 5,685,836 A | 11/1997 | DiPerna et al. | |
| 5,715,815 A | 2/1998 | Lorenzen et al. | |
| 5,775,325 A | 7/1998 | Russo | |
| 5,779,687 A | 7/1998 | Bell et al. | |
| 5,791,337 A | 8/1998 | Coles et al. | |
| 5,836,918 A | 11/1998 | Dondlinger | |
| 5,868,701 A | 2/1999 | Powers, Jr. | |
| 6,068,476 A * | 5/2000 | Point | 433/96 |
| 6,129,547 A | 10/2000 | Cise et al. | |
| 6,258,065 B1 | 7/2001 | Dennis et al. | |
| 6,500,142 B1 | 12/2002 | Harreld et al. | |
| 6,543,451 B1 | 4/2003 | Crump et al. | |
| 6,547,724 B1 | 4/2003 | Soble et al. | |
| 6,588,427 B1 | 7/2003 | Carlsen et al. | |
| 6,632,091 B1 * | 10/2003 | Cise et al. | 433/116 |
| 6,702,789 B1 | 3/2004 | Owens et al. | |
| 6,860,869 B2 | 3/2005 | Dennis | |
| 6,908,428 B2 | 6/2005 | Aizenfeld et al. | |
| 6,923,184 B1 | 8/2005 | Russo et al. | |
| 6,986,773 B1 | 1/2006 | Manougian | |
| 6,997,867 B2 | 2/2006 | Soble et al. | |
| 7,056,303 B2 | 6/2006 | Dennis et al. | |
| 2001/0044600 A1 | 11/2001 | Elkins | |
| 2002/0107484 A1 | 8/2002 | Dennis et al. | |
| 2004/0082923 A1 | 4/2004 | Field | |
| 2004/0171990 A1 | 9/2004 | Dennis et al. | |
| 2004/0182390 A1 | 9/2004 | Owens et al. | |
| 2004/0182393 A1 | 9/2004 | MacMillan et al. | |
| 2004/0186429 A1 | 9/2004 | Owens et al. | |
| 2005/0273063 A1 | 12/2005 | Hoell et al. | |
| 2005/0279359 A1 | 12/2005 | LeBlanc et al. | |
| 2006/0088800 A1 | 4/2006 | Neff et al. | |
| 2006/0100481 A1 | 5/2006 | Soble et al. | |
| 2007/0173764 A1 * | 7/2007 | Greeson et al. | 604/171 |

FOREIGN PATENT DOCUMENTS

| | | |
|---|---|---|
| WO | WO 93/21984 | 11/1993 |
| WO | WO 96/30069 | 10/1996 |

* cited by examiner

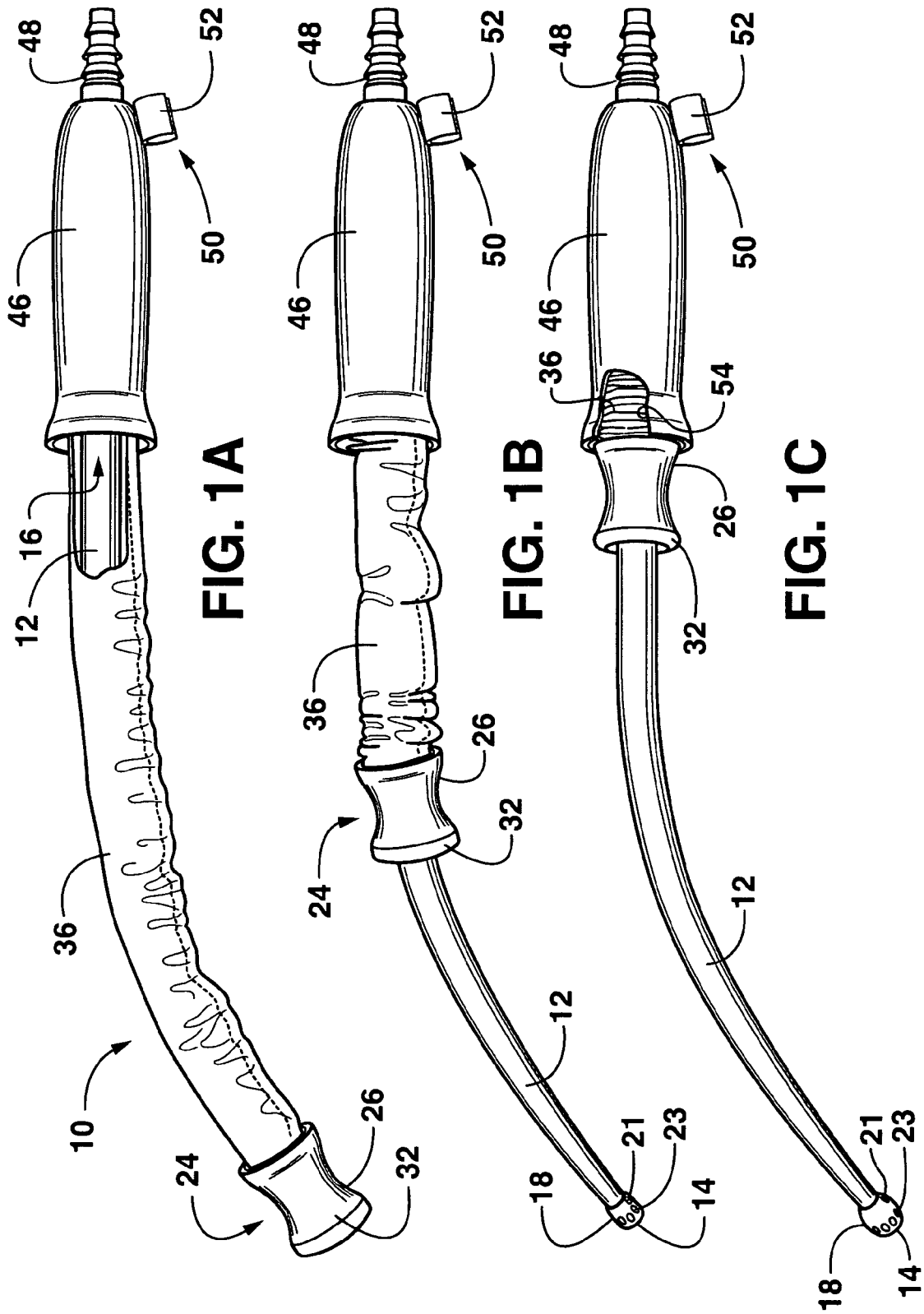

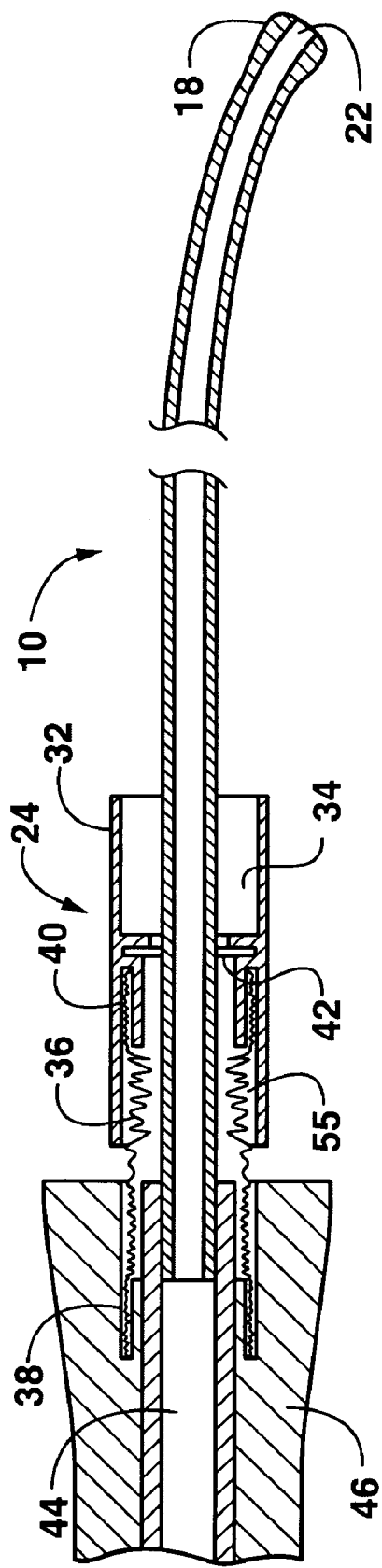
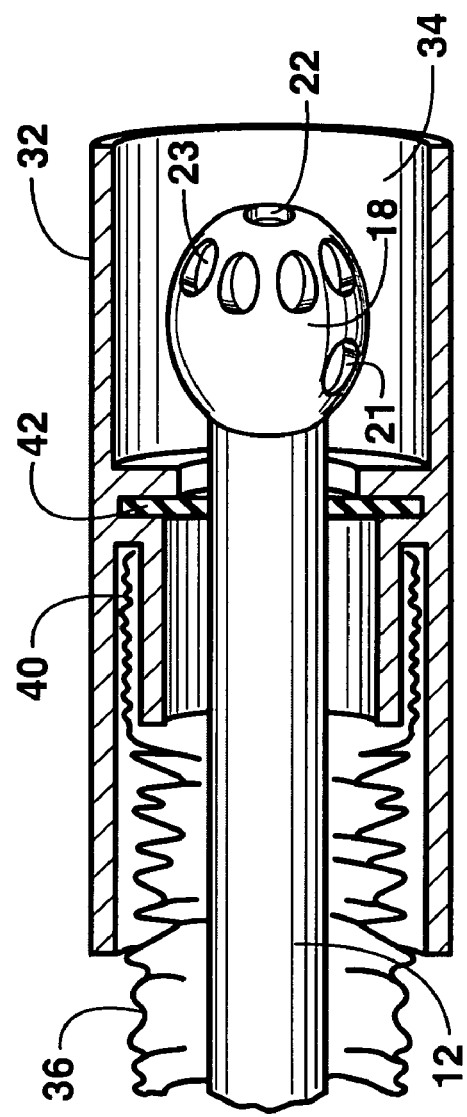
FIG. 3
FIG. 4

YANKAUER SUCTION DEVICE WITH SLEEVE AND WIPER

FIELD OF THE INVENTION

The present invention relates to a medical suctioning device of the type known in the art as a "Yankauer." These devices are typically used to provide suctioning while performing oral care or other procedures on critical care patients.

BACKGROUND

Various medical procedures require suctioning of a patient's mouth. A typical situation is when oral care procedures are performed on an intubated patient. Yankauer suction devices for this purpose are generally known and include an elongated suction tube connectable at one end to a suction source. The other end includes a suction tip with one or more suction holes that is placed in the patient's mouth. The conventional devices suction well and are relatively rigid to allow the clinician to reach remote areas of the mouth that require suctioning.

A concern with the conventional devices is cleanliness and the risk of contamination. The suction devices are typically used for a twenty-four hour period and then disposed of. Between uses, however, the devices must be cleaned and stored in an environment that minimizes the risk of harboring and incubating bacteria from the mouth. This is a burdensome task and, unfortunately, not always followed. The devices typically end up on the floor, are placed on a ledge or other non-sterile surface, or shoved under the patient's pillow wherein they are considered contaminated and must be disposed of. This situation can add substantial cost and inconvenience to the healthcare of the patient.

Attempts have been made to alleviate certain of the problems associated with the Yankauer devices. For example, sheathed devices are know wherein the suction tube is covered by a sleeve or "sheath" between uses. The sheath, however, does not clean the suction tube and may actually foster an environment for rapid growth of bacteria on the surface of the tube. U.S. Pat. No. 6,500,142 describes a suctioning device incorporating a retractable, protective sheath. After use of the device, the clinician slides the sheath forward over the suction tube. The device includes an automatic closure or cap attached to the distal end of the sheath that engages the suction tip and automatically moves to a position to close the cap over the suction tip, essentially isolating the suction tube within the capped sheath. However, unless the suction tube and tip are thoroughly cleaned before deploying the sheath and cap, any bacteria from the patient's mount on the tube and tip will remain and possibly grown, which can lead to re-infection of the patient with subsequent use of the device.

The present invention relates to an improved Yankauer suctioning device that addresses certain of the drawbacks of conventional devices, particularly the sheathed devices.

SUMMARY

Objects and advantages of the invention will be set forth in part in the following description, or may be obvious from the description, or may be learned through practice of the invention.

In accordance with aspects of the invention, a suction device is provided that may be used in any manner of suctioning procedure. The device is particularly suited as a Yankauer suction device for aspirating a patient's mouth, particularly an intubated patient. The device includes an elongated suction tube having a suction tip at a distal end thereof. The proximal end of the suction tube is configured directly or indirectly to any conventional suction source. A collar is disposed around the suction tube and is slidable along the suction tube from a retracted position to a deployed position. A flexible protective sleeve is provided with a proximal end fixed in position relative to the proximal end of the suction tube. The distal end of the sleeve is configured with the collar so as to move therewith and cover the suction tube in the deployed position of the collar. A wiper seal is contained within the collar in sliding frictional engagement around the suction tube. The wiper seal may be formed from any suitable elastomeric material that engages and scrapes along the suction tube as the collar is moved to its deployed position. In this manner, any mucous or particulate matter that accumulates on the exterior of the suction tube from use of the device is effectively scraped from the tube by the wiper seal and moved to the suctioning tip where it can be suctioned through the tip. This cleaning action provides a significant benefit.

In a particular embodiment, the suction device includes a handle member configured at the distal end of the suction tube. The handle member may define a portion of the suction path from the suction source to the suction tube, or may serve to directly couple the suction tube to the suction source. Desirably, the handle includes an adapter for connecting the device to the suction source, or to another intermediary device. The handle may include any manner of additional control features, such as a valve for controlling suction flow through the device. The proximal end of the sleeve can be fixed within the handle member by any suitable means. The handle may also include a storage attachment mechanism configured thereon that provides the clinician with a ready means to store the device between uses. In a particular embodiment, this attachment mechanism may be any suitable clip or like device that allows the device to be attached to suction tubing or other equipment related to the suction source.

In the retracted position of the collar, the sleeve may be stored within a storage recess defined in the collar, or in a storage recess within a handle member configured at the proximal end of the suction tube, so that the sleeve does not interfere with use of the device, and stays clean during such use. Frictional engagement between the wiper seal and the suction tube ensures that the sleeve does not slide freely and stays retracted without necessity of a separate latch or other mechanism to secure the sleeve and collar in the retracted position.

In a particularly unique embodiment, the collar includes an elongated open-ended annular ring portion at the distal end thereof. The suction tip resides within this ring portion in the deployed position of the collar. The ring portion and wiper seal generally define a cleaning chamber within which the suction tip is contained in the deployed position of the collar. To remove any remaining matter from the suction tip after the collar has been slid to the deployed position, the collar may be immersed in a container (e.g., a cup) of cleaning solution. Because the collar is open-ended, the solution is able to circulate within the cleaning chamber and around the suction tip. During this cleaning, suction may be drawn through the suction tip to create a more turbulent cleaning of the tip. Additional suction holes may be provided at a proximal location on the suction tip to further aid in removing any secretions or other matter from the tip or within the cleaning chamber during the cleaning process. The open-ended configuration of the cleaning chamber also promotes good ventilation through and around the suction tip to dry the tip after use or cleaning without the tip coming into contact with external surfaces. This ability to thoroughly clean and dry the suction tip after deploying the sleeve adds additional significant benefits.

The suction tip may take on any desired shape and configuration. In one particular embodiment, the tip comprises a bulbous end with a central orifice and one or more side orifices. As mentioned, any number of additional orifices may be defined in the suction tip to aid in cleaning of the tip. In the deployed position of collar, the wiper seal contacts against the bulbous tip such that further movement of the collar and sleeve is arrested. In an alternate embodiment, the suction tip may be essentially an extension of the suction tube with the same diameter as the tube. In this embodiment, the deployed position of the collar and sleeve may be defined by the length of the sleeve so that the suction tip is not pulled through the wiper seal.

Additional aspects of the invention will be described below by reference to particular embodiments illustrated in the figures.

BRIEF DESCRIPTION OF THE FIGURES

FIGS. 1A through 1C are perspective sequential operational views of an embodiment of a suction device according to the invention.

FIG. 3 is a cross-sectional view of portions of a suction device embodiment according to the invention.

FIG. 4 is a cross-sectional view of the distal end of an embodiment of a suction device according to the invention.

DESCRIPTION

Figure 2A:
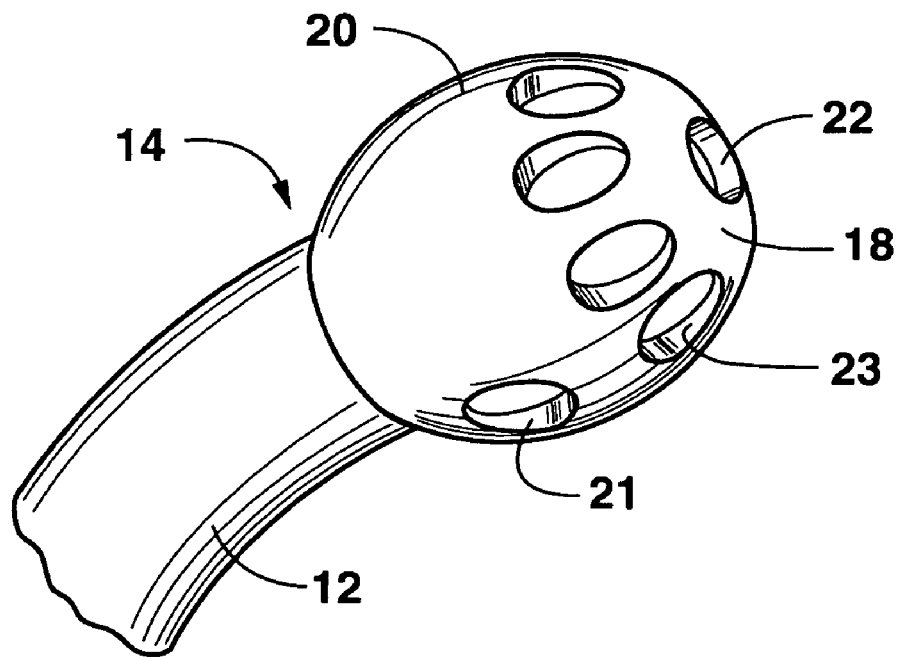
FIGS. 2A and 2B are perspective views of embodiments of suction tips that may be used with devices according to the invention.

Reference will not be made in detail to particular embodiments of the suctioning device, one or more examples of which are illustrated in the drawings. Each embodiment is presented by way of explanation of the invention, and not as a limitation of the invention. For example, features illustrated or described as part of one embodiment may be used with a different embodiment to yield still another embodiment. It is intended that the present invention encompasses these and other modifications and variations as come within the scope and spirit of the invention.

FIGS. 1A through 1C illustrate an embodiment of a suction device 10 in accordance with the invention. The device 10 is particularly suited as a surgical Yankauer device for aspirating a patient's mouth, particularly an intubated patient. The device 10 includes an elongated suction tube 12 having a distal end 14 and a proximal end 16. As used herein, "distal" refers to the direction closest to the patient and "proximal" refers to the direction closest to the clinician. The suction tube 12 includes a suction tip 18 at the distal end 14 thereof.

The proximal end 16 of the suction tube 12 is configured with any conventional suction source typically provided in a medical facility. The suction tube 12 may be configured directly with the suction source, or may be in communication with the suction source through any manner or configuration of intermediate members. Such intermediate members may include any desired functionalities, such as the ability to regulate the suction flow through the device.

The device 10 includes a collar 24 having a body 26 that may be configured with a central recess portion for placement of the clinician's fingers when operating the device 10, as explained below. The collar 24 is disposed around the suction tube 12 and is slidable along the suction tube 12 from a retracted position illustrated in FIG. 1C to a deployed position illustrated in FIG. 1A.

A flexible protective sleeve 36 is disposed around the suction tube 12 and has a proximal end 38 that is fixed relative to the proximal end 16 of the suction tube (FIG. 3). The sleeve 36 has a distal end 40 that is configured with the collar 24 so as to move with the collar between the retracted position of FIG. 1C and the deployed position of FIG. 1A.

Referring to FIGS. 3 and 4, a wiper seal 42 is disposed within the collar 24 and is retained within the collar by any suitable mechanism, such as the recess illustrated in FIGS. 3 and 4. This wiper seal is made from any suitable elastomeric material and is in sliding frictional engagement around the suction tube 12. The wiper seal 42 scrapes along the suction tube 12 as the collar 24 is moved to its deployed position and scrapes any mucous or particulate matter on the suction tube 12 towards the suction tip 18. This matter can then be suctioned away through the tip 18. Frictional engagement between the wiper seal 42 and suction tube 12 may be sufficient to secure the collar at any position along the tube 12. In this manner, in the retracted position of the collar 24 and sleeve 36, an additional latch or other mechanism is not needed to secure the collar relative to the tube 12.

In a particular embodiment of the device 10 illustrated in the figures, a handle member 46 is provided at the distal end 16 of the suction tube 12. The handle member 46 may encompass the tube 12, or include an internal bore 44 that mates with the suction tube 12, as illustrated in FIG. 3. The bore 44 is connectable to any convenient suction source for supplying suction through the suction tube 12. Although not illustrated, it should be understood that the handle 46 may include any manner of functional features, such as a valve or other device to regulate suction flow through the device 10. Desirably, the handle member 46 includes any suitable adapter 48 for connecting the device 10 to the suction source or to any other intermediary member. The adapter 48 may be configured as a universal adapter for insertion into a wide diameter range of external suction tubing. In an alternative embodiment, the adapter 48 may comprise any type of quick release mechanism that mates the apparatus 10 to a suction source or other member. The adapter 48 may include any manner of internal structure to minimize leakage through the connection. For example, the adapter 48 may include an annular flange portion that essentially surrounds an internal connection point so that any leakage from the connection is contained within the annular flange portion.

Referring to FIGS. 1A through 1C, the handle member 46 may also include a storage attachment mechanism 50 that is used to store the device 10 between uses. This storage attachment mechanism 50 may be any type of device, including an adhesive, magnet, mechanical device, and so forth. In the illustrated embodiment, the storage attachment mechanism 50 includes a simple clip 52 sized so as to permit the handle 46 to be attached to any manner of tubing.

Referring to FIG. 1C, in the retracted position of the collar 24, the sleeve 36 may be stored within a recess chamber 54 within the distal end of the handle member 46. In an alternative embodiment illustrated in FIGS. 3 and 4, the sleeve 36 may be stored in a recess 55 within the proximal end of the collar 24. With either embodiment, the sleeve is stowed so as not to interfere with use of the device when the collar 24 is in the retracted position of FIG. 1C. This storage feature also ensures that the sleeve 36 is maintained in a clean environment during use of the device 10.

Figure 2B:
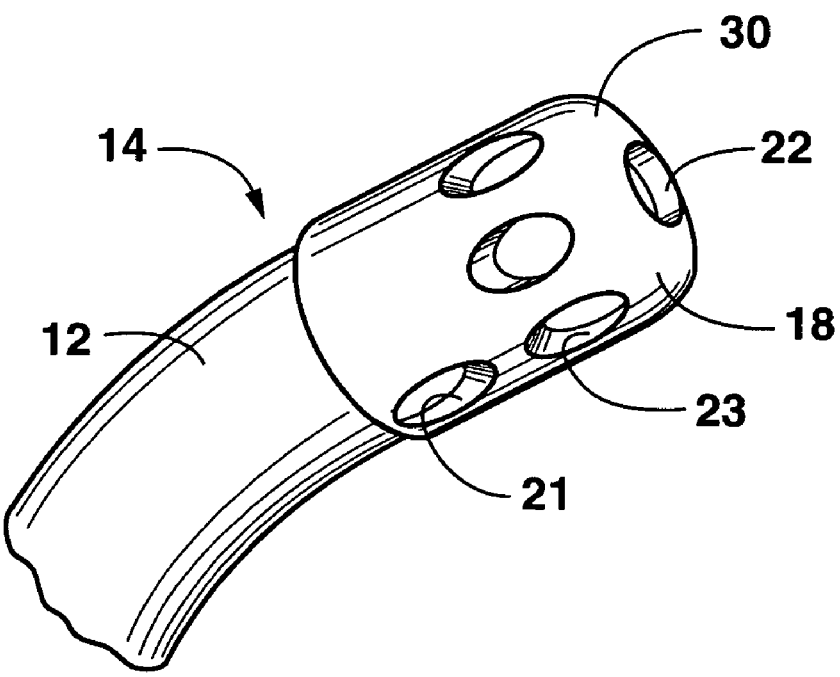
Figure 5:
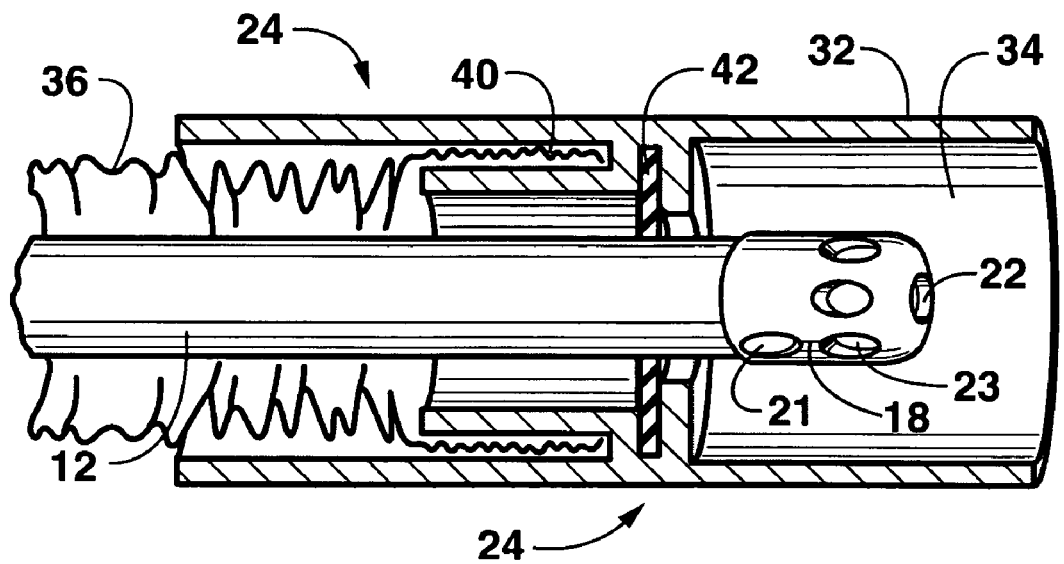
FIG. 5 is a cross-sectional view of the distal end of an alternative embodiment of a suction device according to the invention.

The suction tip 18 of the suction tube 12 may take on any desired shape or configuration. For example, referring to FIGS. 2A and 2B, different embodiments of the suction tip 18 are illustrated. In the embodiment of FIG. 2A, the suction tip 18 includes a bulbous end 20 with a central suction orifice 22 and a plurality of side orifices 23. This configuration may be desired in that the bulbous end 20 presents a rounded non-irritating surface and minimizes any discomfort to the patient. Any configuration of proximally disposed orifices 21 may also be provided to provide a more complete suctioning, as well as to aid in cleaning of the tip 18. In the embodiment of FIG. 2B, the suction tip 18 includes a generally cylindrical body 30 having a central suction orifice 22 and side orifices 23. The cylindrical body 30 may have a diameter that corresponds generally to the diameter of the suction tube 12. This particular embodiment may be desired wherein the device 10 must be used to clean more remote areas that are not accessible by a larger suction tip 18.

The embodiment of the suction tube 12 with the bulbous suction tip 18 is illustrated in FIG. 4. It should be appreciated that, in this particular configuration, the relatively large diameter of the bulbous suction tip 18 prevents the suction tip 12 from being pulled completely through the wiper seal 42 without undue force. Thus, the deployed position of the collar 24 is defined essentially at the location where the wiper seal 42 abuts against the bulbous end 20 of the suction tip 18. In an embodiment wherein the suction tip 18 includes a generally cylindrical body 30 matching the diameter of the suction tube 12, the length of the sleeve 36 can be closely controlled so that the extension length of the sleeve defines the deployed position of the collar 24 at a location so that the suction tip 18 of the suction tube 12 is not pulled completely through the wiper seal 42 and into the protective sleeve.

It should also be appreciated that internal wall or flange structure may be provided within the collar 24 on either sides of the wiper seal 42 to prevent the suction tip 18 from being pulled completely through the collar 24.

Figure 6:
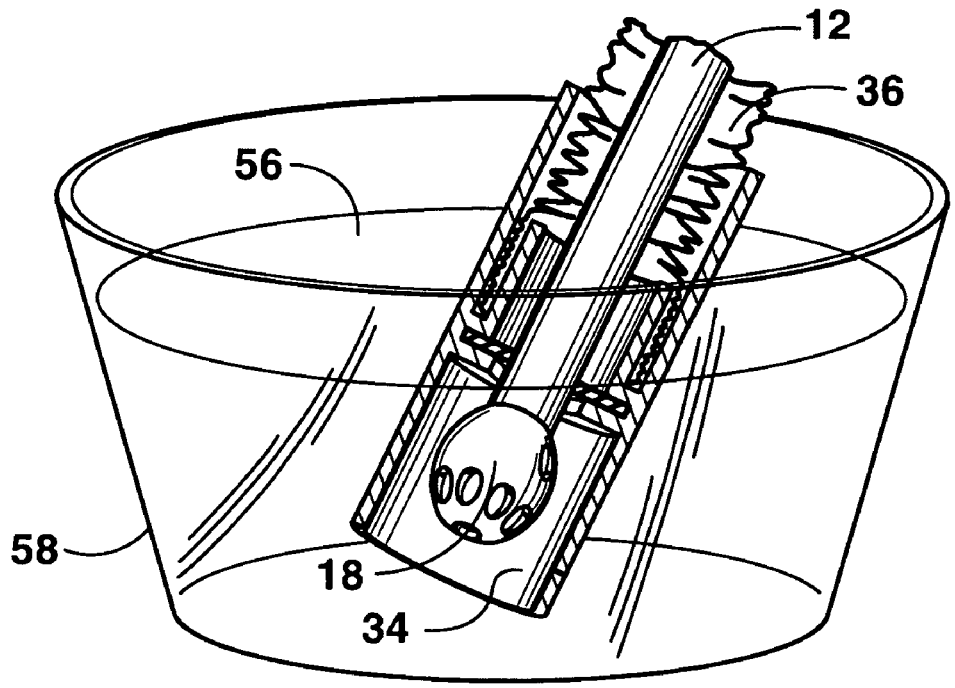
FIG. 6 is a perspective view of a cleaning operation for a suction device according to the invention.

Referring to FIG. 4 in particular, in a particularly unique embodiment of the suction device 10, the collar 24 includes an elongated open-ended annular ring portion 32 at the distal end thereof. This annular ring portion defines a chamber 34 in which the suction tip 18 resides in the deployed position of the collar 24, as illustrated in FIG. 4. The chamber 34, along with the wiper seal 42 defines a cleaning chamber within which the suction tip is contained. Referring to FIG. 6 in particular, a cleaning operation is depicted wherein the distal end of the device 10 with the collar in the deployed position is inverted into a container 58 of cleaning solution 56. The cleaning solution circulates around the suction tip 18 within the chamber 34. To create a more turbulent cleaning action, suction may be applied through the tip 18 while the device is in the cleaning solution. This turbulent cleaning action should suffice to remove any remaining mucous or particulate matter that has been scraped to the suction tip 18 by the action of the wiper seal 42. The proximally oriented suction orifices 21 ensure that any matter that may accumulate at the proximal side of the tip is also removed in the cleaning process.

It should be appreciated that the individual components of the suction device may be made from any suitable combination of materials. For example, the suction tube may be made of any clear medical grade polymer that permits the clinician to view the secretions sucked from the patient. The collar may be made of, for example, a polypropylene material. The wiper seal 42 may be made of any suitable medical grade silicone. The protective sleeve 36 may be made from polyethylene or polypropylene.

It should be readily appreciated by those skilled in the art that modifications and variations can be made to the embodiments of the invention described herein. It is intended that the invention include such modifications as come within the scope and spirit of the invention as set forth in the appended claims.

What is claimed is:

1. A suction device, comprising:
   an elongated suction tube having a suction tip with a bulbous end at a distal end thereof, said suction tube having a proximal end that is connectable to a suction source;
   a collar slidable along said suction tube from a retracted position to a fully deployed position defined by the limit of movement of said collar towards said distal end of said suction tube;
   a sleeve having a proximal end fixed relative to said proximal end of said suction tube, and a distal end configured with said collar so as to move therewith and cover said suction tube in a deployed position of said collar;
   a wiper seal contained within said collar in sliding frictional engagement around said suction tube;
   said collar having an elongated open-ended annular ring portion at a distal end thereof defining an open-ended cleaning chamber in which said suction tip resides in said fully deployed position of said collar; and
   said wiper seal disposed within said collar so that in said fully deployed position of said collar, said wiper seal remains in engagement around said suction tube proximal to said bulbous end of said suction tip such that said bulbous end of said suction tip resides in said cleaning chamber and said wiper seal defines an end of said cleaning chamber in said fully deployed position of said collar.

2. The suction device as in claim 1, further comprising a handle member at said distal end of said suction tube, said handle member comprising a adapter for connecting said suction tube to a suction source, said proximal end of said sleeve fixed within said handle.

3. The suction device as in claim 2, further comprising a storage attachment mechanism configured on said handle.

4. The suction device as in claim 3, wherein said storage attachment mechanism comprises a clip sized to attach said device to the suction source.

5. The suction device as in claim 2, wherein said sleeve is contained with a storage recess in said handle in said retracted position of said collar.

6. The suction device as in claim 1, wherein said sleeve is contained within a storage recess in said collar in said retracted position of said collar.

* * * * *